United States Patent [19]

Scannon et al.

[11] Patent Number: 5,756,464
[45] Date of Patent: May 26, 1998

[54] THERAPEUTIC USES OF BPI PROTEIN PRODUCTS IN HUMANS WITH HEMMORHAGE DUE TO TRAUMA

[75] Inventors: Patrick J. Scannon, San Francisco; Nancy Wedel, Oakland, both of Calif.

[73] Assignee: XOMA Corporation, Berkeley, Calif.

[21] Appl. No.: 927,438

[22] Filed: Sep. 10, 1997

Related U.S. Application Data

[63] Continuation of Ser. No. 652,292, May 23, 1996, abandoned.

[51] Int. Cl.$^6$ .......................... A61K 38/00; A61K 35/14
[52] U.S. Cl. .......................... 514/12; 514/21; 514/921; 530/324; 530/350; 530/829; 424/529; 424/534
[58] Field of Search .......................... 514/12, 21, 921; 530/324, 350, 829; 424/529, 534

[56] References Cited

U.S. PATENT DOCUMENTS

| | | | |
|---|---|---|---|
| 5,089,274 | 2/1992 | Marra et al. | 424/534 |
| 5,171,739 | 12/1992 | Scott et al. | 514/12 |
| 5,198,541 | 3/1993 | Elsbach et al. | 435/69.1 |
| 5,234,912 | 8/1993 | Marra et al. | 514/21 |
| 5,245,013 | 9/1993 | Ulevitch et al. | 530/380 |
| 5,308,834 | 5/1994 | Scott et al. | 514/12 |
| 5,334,584 | 8/1994 | Scott et al. | 514/12 |
| 5,348,942 | 9/1994 | Little, II et al. | 514/12 |
| 5,420,019 | 5/1995 | Theofan et al. | 435/69.1 |
| 5,439,807 | 8/1995 | Grinna | 435/69.1 |
| 5,447,913 | 9/1995 | Ammons et al. | 514/12 |
| 5,466,580 | 11/1995 | White et al. | 435/7.1 |
| 5,466,581 | 11/1995 | White et al. | 435/7.32 |
| 5,484,705 | 1/1996 | White et al. | 435/7.32 |
| 5,488,034 | 1/1996 | McGregor et al. | 514/12 |
| 5,494,896 | 2/1996 | Hansbrough | 514/12 |
| 5,523,288 | 6/1996 | Cohen et al. | 514/12 |
| 5,532,216 | 7/1996 | Espevik et al. | 514/21 |
| 5,576,292 | 11/1996 | Elsbach et al. | 514/12 |
| 5,578,568 | 11/1996 | Ammons et al. | 514/12 |
| 5,578,572 | 11/1996 | Horwitz et al. | 514/12 |

FOREIGN PATENT DOCUMENTS

| | | |
|---|---|---|
| WO 89/01486 | 2/1989 | WIPO. |
| WO 90/09183 | 8/1990 | WIPO. |
| WO 91/01639 | 2/1991 | WIPO. |
| WO 92/03535 | 3/1992 | WIPO. |
| WO 92/09621 | 6/1992 | WIPO. |
| WO 93/05797 | 4/1993 | WIPO. |
| WO 93/06228 | 4/1993 | WIPO. |
| WO 93/23434 | 11/1993 | WIPO. |
| WO 93/23540 | 11/1993 | WIPO. |
| WO 94/17819 | 8/1994 | WIPO. |
| WO 94/18323 | 8/1994 | WIPO. |
| WO 94/20128 | 9/1994 | WIPO. |
| WO 94/20129 | 9/1994 | WIPO. |
| WO 94/20532 | 9/1994 | WIPO. |
| WO 94/21280 | 9/1994 | WIPO. |
| WO 94/25476 | 11/1994 | WIPO. |
| WO 95/00641 | 1/1995 | WIPO. |
| WO 95/01428 | 1/1995 | WIPO. |
| WO 95/02414 | 1/1995 | WIPO. |
| WO 95/08344 | 3/1995 | WIPO. |
| WO 95/08773 | 3/1995 | WIPO. |
| WO 95/10297 | 4/1995 | WIPO. |
| WO 95/19179 | 7/1995 | WIPO. |
| WO 95/19180 | 7/1995 | WIPO. |
| WO 95/19372 | 7/1995 | WIPO. |
| WO 95/19784 | 7/1995 | WIPO. |
| WO 95/20163 | 7/1995 | WIPO. |
| WO 95/24209 | 9/1995 | WIPO. |
| WO 96/01647 | 1/1996 | WIPO. |
| WO 96/08509 | 3/1996 | WIPO. |
| WO 96/21436 | 7/1996 | WIPO. |

OTHER PUBLICATIONS

Abraham and Raffin, "Sepsis Therapy Trials: Continued Disappointment or Reason for Hope?" *JAMA*, 271(23):1876–1878 (Jun. 15, 1994).

ACCP/SCCM Consensus Conference Committee, "American College of Chest Physicians/Society of Critical Care Medicine Consensus Conference: Definitions for sepsis and organ failure and guidelines for the use or innovative therapies in sepsis," *Crit. Care Med.*, 20(6):864–874 (Jun., 1992).

Adjei and Garren, "Pulmonary Delivery of Peptide Drugs: Effect of Particle Size on Bioavailability of Leuprolide Acetate in Healthy Male Volunteers," *Pharmaceutical Research*, 7(6):565–569 (1990).

Agarwal et al., "Blood Transfusion Increases the Risk of Infection After Trauma," *Arch. Surg.*, 128:171–177 (Feb., 1993).

Ammons et al., "Recombinant Amino Terminal Fragment of Bactericidal/Permeability Increasing Protein Prevents Hemodynamic Responses to Endotoxin," *Circulatory Shock*, 41(3):176–184 (Nov., 1993).

Ammons et al., "Protective Effects of an N-Terminal Fragment of Bactericidal/Permeability–Increasing Protein in Rodent Models of Gram–Negative Sepsis: Role of Bactericidal Properties," *J. Infect. Dis.*, 170(6):1473–82 (Dec. 1994).

Ammons et al., "An N-Terminal Fragment of Bactericidal/ Permeability–Increasing Protein Protects against Hemodynamic and Metabolic Derangements in Rat Gram–Negative Sepsis," *J. Endotoxin Res.*, 3(1):57–66 (1996).

Ammons et al., "Protective Effects of an N–Terminal Fragment of Bactericidal/Permeability–Increasing Protein in Endotoxemia and Gram–Negative Sepsis," *Novel Therapeutics Strategies in the Treatment of Sepsis*, pp. 55–70 (1996).

Baggiolini et al., "Neutrophil–activating Peptide–1/Interleukin 8, a Novel Cytokine That Activates Neutrophils," *J. Clin. Invest.*, 84:1045–1049 (Oct., 1989).

(List continued on next page.)

*Primary Examiner*—Cecilia J. Tsang
*Assistant Examiner*—Abdel A. Mohamed
*Attorney, Agent, or Firm*—Marshall, O'Toole, Gerstein, Murray & Borun

[57] ABSTRACT

Methods and materials for the treatment of humans suffering from hemorrhage due to trauma are provided, in which therapeutically effective amounts of BPI protein products are administered.

5 Claims, No Drawings

OTHER PUBLICATIONS

Bahrami et al., "Endotoxemia in Rats Subjected to the Hemorrhage: Effects of Bacteriocidal/Permeability Increasing Protein (BPI)," presentation at Vienna International Endotoxin Society Meeting, 1 page (Aug., 1992).

Barron, "Clinical Frontiers: Pathophysiology of Septic Shock and Implications for Therapy," *Clinical Pharmacy*, 12(11):829–845 (Nov., 1993).

Berg, R. D., "Bacterial Translocation From The Gastrointestinal Tract,"*J. of Medicine*, 23(3 & 4):217–244 (1992).

Berry, L. J. (Ed.), "Cellular Biology of Endotoxin," *Handbook of Endotoxin*, vol. , Elsevier, New York, pp. xvii–xxi (1985).

Bickell et al., "Immediate Versus Delayed Fluid Resuscitation for Hypotensive Patients With Penetrating Torso Injuries," *New Engl. J. Med.*, 331(17):1101–1109 (Oct. 27, 1994).

Bigatello et al., "Endotoxemia, Encephalopathy, and Mortality in Cirrhotic Patients," *Amer. J. Gastroenterology*, 82(1)L11–15 (1987).

Binnema et al., "Quantitation of Urokinase Antigen in Plasma and Culture Media by Use of an Elisa," *Throm. Res.*, 43:569–577 (1986).

Bloom et al., "Serum Neopterin Levels Following Intravenous Endotoxin Administration to Normal Humans," *Immunobiol.*, 181:317–323 (1990).

Boermeester et al., "Bactericidal/permeability–increasing protein (BPI) prevents hemodynamic and metabolic derangements following partial hepatectomy," presented at Dutch Society of Gastroenterology Meeting, p. 84 (Oct. 7, 1993) (Abstract).

Boermeester et al., "A Prophylactic Approach towards Postoperative Endotoxemia," *Yearbook of Intensive Care and Emergency Medicine 1994*, Vincent, J. L., (Ed.), Springer–Verlag, New York, pp. 35–41 (1994).

Boermeester et al., "Endotoxin and Interleukin–1 Related Hepatic Inflammatory Response Promotes Liver Failure After Partial Hepatectomy," *Hepatology*, 22:1499–1506 (1995).

Boermeester et al., "Liver Failure Induces a Systemic Inflammatory Response," *Amer. J. Pathology*, 147(5):1428–1440 (Nov., 1995).

Bone et al., "Definitions for Sepsis and Organ Failure," *Critical Care Medicine*, 20(6):724–726 (1992).

Boujoukos et al., "Detection of Interleukin–8 in Bronchoalveolar Lavage Without Alveolar Neutrophil Influx, Before and After Intravenous Endotoxin in Normal Humans," *Am. Rev. Resp. Dis.*,145(4):A441 (Apr., 1992) (Abstract).

Boujoukos et al., "Compartmentalization of the Acute Cytokine Response in Humans After Intravenous Endotoxin Administration," *J. Appl. Physiol.* 74:3027–3033 (1993).

Bradley et al., "Hemodynamic Alterations in Normotensive and Hypertensive Subjects During the Pyrogenic Reaction, "*J. Clin. Invest.*, 24:749–758 (1945).

Brathwaite et al., "Bacterial Translocation Occurs in Humans After Traumatic Injury: Evidence Using Immunofluorescence," *J. Trauma*, 34(4):586–590 (1993).

Braunwald et al., *Heart Disease, The Textbook of Cardiovascular Medicine*, 3rd Edition, Braunwald, E., (Ed.), W.B. Saunders Company, Harcourt Brace Jovanich, Inc., Philadelphia, PA, p. 12 (1988).

Brigham et al., "Endotoxin and Lung Injury," *Rev. Respir. Dis.*, 133:913–927 (1986).

Calandra et al., "Prognostic Values of Tumor Necrosis Factor/Cachectin, Interleukin–1, Interferon–α, and Interferon–µ in the Seurm of Patients with Septic Shock," *J. Infectious Diseases*, 161:982–987 (1990).

Calandra et al., "High Circulating Levels of Interleukin–6 in Patients with Septic Shock: Evolution During Sepsis, Prognostic Value, and Interplay with Other Cytokines," *Am. J. Medicine*, 91:23–29 (Jul. 1991).

Canon et al., "Circulating Interleukin 1 and Tumor Necrosis Factor in Septic Shock and Experimental Endotoxin Fever, "*J. Infection Diseases*, 161:79–84 (1990).

Captopril–Digoxin Multicenter Research Group, "Comparative Effects of Therapy With Captopril and Digoxin in Patients With Mild to Moderate Heart Failure," *JAMA*, 259(4):539–544 (Jan. 22/29 1988).

Carrico et al., "What's New in Trauma and Burns," *Bulletin of the American College of Surgeons* 80(1)71–74 (1995).

Cavaillon, J. M., "Controversies Surrounding Current Therapies For Sepsis Syndrome," *Bull. Inst. Pasteur.*, 93:21–41 (1995).

Champion et al., "Trauma Score," *Crit. Care Med.*, 9(9):672–676 (Sep., 1981).

Chimielewska et al., "Evidence for a Rapid Inhibitor Tissue Plasminogen Activator in Plasma," *Thromb. Res.*, 31:427–436 (1983).

Cochrane, "The Enhancement of Inflammatory Injury," *Am. Rev. Respir. Dis.*, 136:1–2 (1980).

Colman, "Surface–mediated Defense Reactions, The Plasma Contact Activation System," *J. Clin. Invest.*, 73:1249–1253 (May 1984).

Cross, A.S., "Antiendotoxin Antibodies: A Dead End?" *Annals of Internal Medicine*, 121(1):58–60 (Jul. 1, 1994).

Danner et al., "Endotoxemia in Human Septic Shock," *Chest*, 99:169–175 (Jan., 1991).

Deitch, E.A., "The Role of Intestinal Barrier Failure and Bacterial Translocation in the Development of Systemic Infection and Multiple Organ Failure," *Arch Surg* 125:403–404 (Mar., 1990).

Deitch, E.A., "Multiple Organ Failure: Pathophysiology and Potential Future Therapy," *Ann. Surg.*, pp. 117–134 (Aug., 1992).

DeLa Cadena et al., "Activation of the Kallikrein–Xn System After Endotoxin Administration to Normal Human Volunteers," *Blood*, 81(12):3313–3317 (Jun. 15, 1993).

Dinarello, "The Proinflammatory Cytokines Interleukin–1 and Tumor Necrosis Factor and Treatment of the Septic Shock Syndrome," *J. Infection Diseases*, 163:117–1184 (1991).

Duke et al., "Transfusion Significantly Increases the Risk for Infection After Splenic Injury," *Arch. Surg.*, 128:1125–1132 (1993).

Elin et al., "Effect of Induced Fever on Serum Iron and Ferritin Concentrations in Man," *Blood*, 49(1):147–153 (Jan. 1977).

Elms et al., "Measurement of Crosslinked Fibrin Degradation Products—An Immunoassay Using Monoclonal Antibodies" *Thromb. Haemostasis*, 50(2):591–594 (1983).

Elsbach et al., "Separation and Purification of a Potent Bactericidal/Permeability Increasing Protein and a Closely Associated Phospholipase A2 from Rabbit Polymorphonuclear Leukocytes," *J. Biol. Chem.*, 254:11000 (1979).

Elsbach et al., "Oxygen–Independent Antimicrobial Systems of Phagocytes" *Inflammation: Basic Principles and Clinical Correlates*, Chapter 30, pp. 603–636, 2nd. Edition, Gallen et al., (Eds.) Raven Press Ltd., (1992).

Elsbach and Weiss, "Prospects for Use of Recombinant BPI in the Treatment of Gram–Negative Bacterial Infections," *Infectious Agents and Disease*, 4:102–109 (1995).

Evans et al., "Protective Effects of a Recombinant Amino-–Terminal of Human Bactericidal/Permeability–Increasing Protein in an Animal Model of Gram–Negative Sepsis," *J. Infect. Dis.*, 171:153–60 (Jan., 1995).

Fink, M. P., "Adoptive Immunotherapy of Gram–Negative Sepsis: Use of Monoclonal Antibodies to Lipopolysaccharide," *Critical Care Medicine, Supplement* 21(2):S32–S39 (1993).

Fisher et al., "Human Neutrophil bactericidal/permeability–increasing protein reduces mortality rate from endotoxin challenge: A placebo–controlled study," *Critical Care Med.,* 22(4):553–558 (Apr., 1994).

Fisher et al., "Recombinant Human Interleukin 1 Receptor Antagonist in the Treatment of Patients With Sepsis Syndrome," *JAMA,* 271(23):1836–1843 (Jun. 15, 1994).

Fong et al., "Endotoxemia Elicits Increased Circulating B2–IFN/IL–6 in Man," *J. Immunology,* 142(7):2321–2324 (Apr. 1, 1989).

Fong et al., "Total Parental Nutrition and Bowel Rest Modify the Metabolic Response to Endotoxin in Humans," *Ann. Surg.,* 210:449–457 (1989).

Fong et al., "The Acute Splanchnic and Peripheral Tissue Metabolic Response to Endotoxin in Humans," *J. Clin. Invest.,* 85:1896–1904 (1990).

Gazzano–Santoro et al., "High–Affinity Binding of the Bactericidal/Permeability–Increasing Protein and a Recombinant Amino–Terminal Fragment to the Lipid A Region of Lipopolysaccharide," *Infect. Immun.* 60(11):4754–4761 (Nov., 1992).

Goris et al., "Multiple–Organ Failure: Generalized Autodestructive Inflammation?" *Arch Surg.,* 120:1109–1115 (Oct., 1985).

Granowitz et al., "Production of interleukin–1–receptor antagonist during experimental endotoxaemia," *Lancet,* 338:1423–24 (1991).

Granowitz et al., "Hematologic and Immunomodulatory Effects of an Interleukin–1 Receptor Antagonist Contusion During Low–Dose Endoxemia in Healthy Humans," *Blood,* 82(10):2985–2990 (1993).

Gray et al., "Cloning of the cDNA of a Human Neutrophil Bactericidal Protein," *J. Biol. Chem.,* 264(16):9505–9509 (Jun. 5, 1989).

Greenfield et al., (Eds.), In: *Surgery Scientific Principles and Practices,* Chapter 10.J.B. Lippincott Co., Philadelphia, pp. 252–255 (1993).

Hack et al., "A Modified Competitive Inhibition Radioimmunoassay for the Detection of C3a," *J. Immunol. Meth.,* 108:77–84 (1988).

Hesse et al., "Cytokine Appearance in Human Endotoxemia and Primate Bacteremia," *Surg., Gyn., & Obstet.,* 166:147–153 (Feb., 1988).

Hochberg, Y., "A sharper Bonferroni procedure for multiple tests of significance," *Biometrika,* 75(4):800–802 (1988).

Hoffman et al., "Endotoxin in Septic Shock," *Anesth. Analg.,* 77:613–624 (1993).

Holvoet, P. et al., "Assay of Human Tissue–Type Plasminogen Activator (t–PA) with an Enzyme–Linked Immunosorbent Assay (ELISA) Based on Three Murine Monoclonal Antibodies to t–PA," *Thromb. Haemostasis,* 54(3):684–687 (1985).

In 't Veld, "Effects of the Bactericidal/Permeability–Increasing Protein of Polymorphonuclear Leukocytes on Isolated Bacterial Cytoplasmic Membrane Vesicles," *Infect. Immun.,* 56(5):1203–1208 (1988).

Kelly et al., "Role of the Bactericidal Permeability–increasing Protein in the Treatment of Gram–negative Pneumonia," *Surgery,* 114(2):140–146 (Aug., 1993).

Kindt et al., "Initial Recruitment of Neutrophils to Alveolar Structures in Acute Lung Injury," *J. Appl. Physiol.,* 70:1575–1585 (1991).

Koch, G.G., "The Use of Non–Parametric Methods in the Statistical Analysis of the Two–Period Change–Over Design," *Biometrics,* 28:577–584 (Jun., 1972).

Kohn et al., "Protective Effect of a Recombinant Amino–Terminal Fragment of Bactericidal/Permeability–Increasing Protein in Experimental Endotoxemia," *J. Infect. Diseases,* 166(5):1307–1310 (Nov., 1993).

Kohn et al., "Role of Endotoxin in Acute Inflammation Induced by Gram–Negative Bacteria:Specific Inhibition of Lipopolysaccharide–Mediated Responses with an Amino–Terminal Fragment of Bactericidal/Permeability–Increasing Protein," *Infect. Immun.,* 63(1):333–339 (Jan., 1995).

Koyama et al., "rBPI$_{23}$ Attenuates Endotoxin–Induced Cardiovascular Depression in Awake Rabbits," *SHOCK,* 4(1):74–78 (Jul., 1995).

Kung et al., "Pharmacokinetic Evaluations of rBPI$_{23}$ in Mice, Rats, Rabbits, and Humans," International Conference on Endotoxemia IV, Amsterdam, The Netherlands, Academic Medical Center, p. 23 (Aug. 17–29, 1993) (Abstract P3).

Kung et al., "Efficacy of a Recombinant Terminal Fragment of Bactericidal/Permeability Increasing Protein in Rodents Challenged with LPS or *E. coli* Bacteria," In *Bacterial Endotoxins: Basic Science to Anti–Sepsis Strategies,* Wiley–Liss, New York, pp. 255–263 (1994).

Leach et al., "Prevention of Lethal Endotoxemia by BP$_{23}$. A Recombinant 23 KD LPS–Binding Fragment of Bactericidal/Permeability Increasing Protein (BPI)," *J. Cell. Biochem, Keystone Symposia on Molecular & Cellular Biolgy, Suppl.* 16(C):172 (Feb. 21 Mar. 7, 1992) (Abstract CB 412).

Lechner et al., "the Recombinant 23–kDa N–Terminal Fragment of Bactericidal/Permeability–Increasing Protein (rBPI$_{23}$) Decreases *Escherichia coli*–Induced Mortality and Organ Injury During Immunosuppression–Related Neutropenia," *SHOCK,* 4(4):298–306 (Nov., 1995).

Levi et al., "Reduction of Contract Activation Related Fibrinolytic Activity in Factor XII Deficient Patients," *J. Clin. Invest.,* 88:1155–1160 (Oct., 1991).

Levy et al., "Antibacterial 15–kDa Protein Isoforms (p15s) Are Members of a Novel Family of Leukocyte Proteins,"*J. Biol. Chem.,* 268:6058–6063 (1993).

Lichtman et al., "Reactivation of Arthritis Induced by Small Bowel Bacterial Overgrowth in Rats: Role of Cytokines, Bacteria, and Bacterial Polymers," *Infect. Immun.,* 63(6):2295–2301 (Jun., 1995).

Lin et al., "Protective Effect Of A Recombinant Fragment Of Bactericidal/Permeability Increasing Protein Against Carbohydrate Dyshomeostasis And Tumor Necrosis Factor–α Elevation In Rate Endotoxemia," *Biochem. Pharmacol.* 47(9):1553–1559 (Apr., 1994).

Lin et al., "Protective Effects of a Recombinant N–Terminal Fragment of Bactericidal/Permeability Increasing Protein on Endotoxic Shock in Conscious Rabbits," *SHOCK,* 2(5):324–331 (Nov., 1994).

Lin et al., "Synergistic Effect of a Recombinant N–Terminal Fragment of Bactericidal/Permeability–Increasing Protein and Cefamandole in Treatment of Rabbit Gram–Negative Sepsis," *Antimicrobial Agents and Chemotherapy,* 40(1):65–69 (Jan., 1996).

Lumsden et al., "Endotoxin Levels Measured by a Chromogenic Assay in Portal, Hepatic and Peripheral Venous Blood in Patients with Cirrhosis," *Hepatology,* 8(2):232–236 (1988).

MacIntyre et al., "E5 Antibody Improves Outcome from Multi–Organ Failure in Survivors of Gram–Negative Sepsis," *Critical Care Medicine,* p. S14 (Apr., 1991).

Mannion et al., "Separation of Sublethal and Lethal Effects of Polymorphonuclear Leukocytes on *Escherichia coli*," *J. Clin. Invest.*, 86:631–641 (Aug., 1990).

Marra et al., "Bactericidal/Permeability–Increasing Protein Has Endotoxin–Neutralizing Activity. " *J. Immunol*, 144(2):662–666 (Jan. 15, 1990).

Marra et al., "The Role of Bactericidal/Permeability–increasing Protein as a Natural Inhibitor of Bacterial Endotoxin," *J. Immunol.*, 148(2):532–537 (Jan. 15, 1992).

Marra et al., "Endotoxin–binding and –neutralizing properties of recombinant bactericidal/permeability–increasing protein and monoclonal antibodies HA–1A and E5," *Critical Care Med.*, 22(4):559–565 (1994).

Martich et al., "Detection of Interleukin 8 and Tumor Necrosis Factor in Normal Humans after Intravenous Endotoxin: The Effect of Antiinflammatory Agents," *J. Exp. Medicine*, 173:1021–1024 (Apr., 1991).

Martich et al., "Effects of Ibuprofen and Pentoxifylline on the Cardiovascular Response of Normal Humans to Endotoxin," *J. Appl. Physiol.*, 73:925–931 (1992).

Martich et al., "Intravenous Endotoxin Administration to Normal Humans Primes Neutrophils for an Enhanced Respiratory Burst," *Critical Care Medicine*, p. S100 (Apr., 1992) (Abstract).

Martich et al., "Response of Man to Endotoxin," *Immunobiol.*, 187:403–416 (Apr., 1993).

Mèszàros, "A Recombinant Amino Terminal Fragment of Bactericidal/Permeability–Increasing Protein Inhibits Induction of Leukocyte Responses by LPS," *J. Leukocyte Biol.*, 54(6):558–563 (Dec., 1993).

Michie et al., "Detection of Circulating Tumor Necrosis Factor After Endotoxin Administration," *N. Eng. J. Medicine*, 318(23):1481–1486 (Jun. 9, 1988).

Moore et al., "A Single Dose of Endotoxin Activates Neutrophils without Activating Complement," *Surgery*, 102:200–205 (Feb. 12–14, 1987).

Moser et al., "Cardiopulmonary Consequences of Pyrogen––Induced Hyperpyrexia in Man," *J. Clin. Invest.*, 43(5):626–634 (1963).

Nakagawa et al., "Activation of Reticuloendothelial Function for Prevention of Endotoxemia after Hepatectomy in Cirrhotic Patients," *Tohoku J. exp. Med.*, 153:133–136 (1987).

Natanson et al., "Role of Endotoxemia in Cardiovascular Dysfunction and Mortally," *J. Clin. Invest.*, 83:243–251 (Jan., 1989).

Nolan, J.P. "Progress in Hepatology: The Role of Endotoxin in Liver Injury," *Gastroenterology*, 69(6):1346–1356 (1975).

Nolan, J.P., "Endotoxin, Reticuloendothelial Function, and Liver Injury," *Hepatology*, 1(5):458–465 (1981).

Nuijens et al., "Plasma Elastase α1–antitrypsin and lactoferrin in sepsis: Evidence of neutrophils as mediators in fatal sepsis," *J. Lab. Clin. Med.*, 119:159–168 (1992).

Ooi et al., "A 25–kDa NH$_2$–terminal Fragment Carries All the Antibacterial Activities of the Human Neutrophil 60–kDa Bactericidal/Permeability–increasing Protein," *J. Biol. Chem.*, 262(31):14891–14894 (1987).

Ooi et al., "Isolation of Two Isoforms of a Novel 15–kDa Protein from Rabbit Polymorphonuclear Leukocytes that Modulate the Antibacterial Actions of Other Leukocyte Proteins," *J. Biol. Chem.*, 265:15956–15962 (Sep. 15, 1990).

Ooi et al., "Endotoxin neutralizing Properties of the 25 kD N–Terminal Fragment and a Newly Isolated 30kD C–Terminal Fragment of the 55–60 kD Bactericidal/Permeability–increasing Protein of Human Neutrophils," *J. Exp. Med.*, 174:649–655 (Sep., 1991).

Parker et al., "Profound but Reversible Myocardial Depression in Patients with Septic Shock," *Ann. Intern. Med.*, 100:483–490 (1984).

Parker et al., "Serial cardiovascular variables in survivors and nonsurvivors of human septic shock: Heart rate as an early predictor of prognosis," *Crit. Care Med.*, 15(10):923–929 (1987).

Parrillo et al., "Septic Shock in Humans," *Annals of Intern. Med.* 1133:227–242 (Aug., 1990).

Peters et al., "Rapid Microanalysis of Coagulation Parameters by Automated Chromogenic Substrated Methods–Application in Neonatal Patients," *Thromb. Res.*, 28:773–781 (1982).

Peitzman et al., "Bacterial Translocation in Trauma Patients," *J. Trauma*, 31(8):1083–1087 (1991).

Petros, "Efforts of a Nitric Oxide Synthase Inhibitor in Humans with Septic Shock," *Cardiovascular Res.*, 28:34–39 (1994).

Pruzanski et al., "Hyperphospholipasemia A$_2$ in Human Volunteers Challenged with Intravenous Endotoxin," *Inflammation*, 16(5):561–570 (1992).

Quezado et al., "A Controlled Trial of HA–1A in a Canine Model of Gram–Negative Septic Shock,"JAMA, 269(17):2221–2227 (May 5, 1993).

Quezado et al., "New Strategies for Combatting Sepsis: the Magic Bullets Missed the Mark . . . But the Search Continues," *TribTech*, 13:56–63 (Feb., 1995).

Rackow et al., "Hemodynamic Response to Fluid Repletion in Patients With Septic Shock: Evidence for Early Depression of Cardiac Performance," *Circ. Shock*, 22:11–22 (1987).

Revhaug et al., "Inhibition of Cyclo–oxygenase Attenuates the Metabolic Response to Endotoxin in Humans," *Arch. Surg.* 123:162–170 (Feb., 1988).

Roumen et al., "Cytokine Patterns in Patients After Major Vascular Surgery, Hemorrhage Shock, and Severe Blunt Trauma: Relation with Subsequent Adult Respiratory Distress Syndrome and Multiple Organ Failure," *Annals of Surgery*, 218(6):769–776 (1993).

Roumen et al., "Inflammatory Mediators in Relation to the Development of Multiple Organ Failure in Patients After Severe Blunt Trauma," *Critical Care Med.*, 23(3):474–480 (1995).

Saadia et al., "Gut Barrier Function and the Surgeon," *Br. J. Surg.*, 77:487–492 (May, 1990).

Sawyer et al., "Antimicrobial Therapy of Intra–Abdominal Sepsis," *Surgical Infections, Infectious Disease Clinics of North America*, 6(3):545–570 (Sep. 1992).

Scannon, P. J., "Applying Lessons Learned from Anti–Endotoxin Therapy," *J. Endotoxin Research.*, 2:217–220 (1995).

Schlag et al., "Protective Effect of Bactericidal/Permeability–Increasing Protein (BPI$_{21}$) on Sepsis Induced Organ Failure in Nonhuman Primates," *SHOCK* Conference, Ashville, N.C. Jun. 11–14, 1995, (1995) (Abstract).

Setrakain et al., "Reduced Tumor Necrosis Factor α Production in Lipopolysaccharide–Treated Whole Blood Form Patients in the Intensive Care Unit," *Arch Surg*, 129:187–192 (Feb., 1994).

Smith et al., "Endotoxin Administration to Normal Human Causes Increased Alveolar Permeability and Priming of Alveolar Macrophages to Produce Enhanced Superoxide and IL–1 Production," *Clin. Res*, 36(3):374A (Apr., 1988) (Abstract).

Spinas et al, "Induction of plasma inhibitors of interleukin 1 and TNF–α activity by endotoxin administration to normal humans," *Am. J. Physiol.*, 259:R933–R997 (1990).

Spinas et al."Pretreatment with Ibuprofen Augments Circulating Tumor Necrosis Factor–α, Interleukin–6, and Elastase during Acute Endotoxinemia." *J. Infectious Dis.*, 163:89–95 (1991).

Sturk et al., "Optimalization of a Chromogenic Assay for Endotoxin in Blood," in *Progress in Clinical and Biological Research volume189, Bacterial Endotoxins: Structure, Biomedical Significance, and Detection with the Limulus Amebocyte Lysate Test*, ten Cate et al., (Eds.), Alan R. Liss, Inc., New york. pp. 117–136 (1985).

Suffredini et al., "Promotion and Subsequent Inhibition of Plasminogen Activation after Administration of Intravenous Endotoxin to Normal Subjects," *N. Eng. J. Medicine*, 320(18):1165–1172 (May 4, 1989).

Suffredini et al., "The Cardiovascular Response of Normal Humans to the Administration of Endotoxin," *N. Eng. J. Medicine*, 321:280–287 (Aug. 3, 1989).

Suffredini et al., "Pulmonary and Oxygen Transport Effects of Intravenously Administered Endotoxin in Normal Humans," *Am. Rev. Respir. Dis.*, 145:1398–1403 (1992).

Suffredini, A. F., "Current Prospects for the Treatment of Clinical Sepsis, " *Critical Care Medicine*, 22(7):S12–S18 (Jul., 1994).

Teasdale et al., "Assessment of Coma and Impaired Consciousness," *Lancet*, 1:81–83 (Jul., 1974).

Teitel et al., "Studies of the Prothrombin Activation Pathway Utilizing Radioimmunoassays for the $F_2/F_{1+2}$ Fragment and Thrombin–Antithrombin Complex," *Blood*, 59(5):1086–1096 (May, 1982).

Thompson et al., "Major Hepatic Resection," *Annals of Surgery*, 197(4):375–388 (Apr., 1983).

Tran et al., "Risk Factors for Multiple Organ System Failure and Death in Critically Injured Patients," *Surgery*, 114:21–30 (1993).

Trunkey, D.D., "Trauma," *Sci. Amer.*, 249(2):28–35 (Aug., 1983).

Trunkey, D.D., "Initial Treatment of Patients with Extensive Trauma," *New Eng. J. Med.*, 324(18):1259–1263 (May, 1991).

van Deventer et al., "Experimental Endotoxemia in Humans: Analysis of Cytokine Release and Coagulation, Fibrinolytic, and Complement Pathways," *Blood*, 76(12):2520–2526 (Dec. 15, 1990).

van Leeuwan et al., "Hepatic Failure and Coma After Liver Resection is Reversed by Manipulation of Gut Contents: The Role of Endotoxin," *Surgery*, 110(2):169–175 (Aug., 1991).

Van Leeuwen et al., "Clinical Significance of Translocation," *Gut, Supplement* 1:S28–S34 (1994).

Van Zee et al., "Tumor Necrosis Factor Soluble Receptors Circulate during Experimental and Clinical Inflammation and Can Protect Against Excessive Tumor Necrosis Factor, α in vitro and in vivo," *Proc. Natl. Acad. Sci. USA.*, 89:4845–4849 (Jun., 1992).

Van Zee et al., "Tumor Necrosis Factor (TNF) Soluble Receptors Protect Against Excessive TNFα During Infection and Injury," *Fed. Amer. Soc. Exp. Biol.*, 6:A1715 (1992).

VanderMeer et al., "Bactericidal/Permeability–Increasing Protein Ameliorates Acute Lung Injury in Porcine Endotoxemia," *J. Infect. Dis.*, 172(1):2006–14 (May 1994).

Verheijen et al., "A Simple, Sensitive Spectrophotometric Assay for Extrinsic (Tissue–Type) Plasminogen Activator Applicable to Measurements in Plasma," *Thromb. Haemostas*, 48(3):266–269 (1982).

von der Mohlen et al., "Effect of rBPI23 on Endotoxin–Induced Cytokine Release and Leukocyte Changes in Human Volunteers," *Clinical Research*, 42(2):152A (Apr., 1994) (Abstract).

Waage et al., "The Complex Pattern of Cytokines in Serum from Patients with Meningococcal Septic Shock, " *J. Exp. Med.* 169:333–338 (Jan., 1989).

Weiss et al., "Resistance of Gram–negative Bacteria to Purified Bactericidal Leukocyte Proteins," *J. Clin. Invest.*, 65:619–628 (Mar., 1980).

Weiss et al., "The Role of Lipopolysaccharide in the Action of the Bactericidal/Permeability–Increasing Neutrophil Protein on the Bacterial Envelope," *J. Immunol.*, 132(6):3109–3115 (Jun., 1984).

Weiss et al., "Cellular and Subcellular Localization of the Bactericidal/Peremability–Increasing Protein of Neutrophils," *Blood*, 69:652 (Feb., 1987).

Weiss et al., "Tissue Destruction by Neutrophils," *N. Eng. J. Medicine*, 320(6):365–376 (Feb. 9, 1989).

Weiss et al., "Human Bactericidal/Permeability–Increasing Protein and a Recombinant $NH_2$–Terminal Fragment Cause Killing of Serum–Resistant Gram–Negative Bacteria in Whole Blood and Inhibit Tumor Necrosis Factor Release Induced by the Bacteria," *J. Clin. Invest.*, 90:1122–1130 (Sep., 1992).

Wolff, "Biological Effects of Bacterial Endotoxins in Man," J. Infectious Diseases 128(Supplement): S259–S264 (Jul., 1973).

Yong et al., "An Experimental Mouse Model of Yersinia–Induced Reactive Arthyritis," *Microbial Pathogenesis*, 4:305–310 (1988).

Yong et al., "Protective Effect of Re–LPS Antiserum on experimental Multiple System Organ Failure," *Chinese Medical Journal*, 105(10):833–838 (Oct., 1992).

Zabel et al., "Oxpentifylline in Endotoxaemia," *Lancet*, 2:1474–1477 (Dec. 23/30, 1989).

De Winter et al, *Journal of Inflammation*, vol. 45, pp. 193–206, 1995.

Cross et al, *Infection and Immunity*, vol. 61, No. 7, pp. 2741–2747, 1993.

Fink et al, *Journal of Surgical Research*, vol. 49, pp. 186–196, 1990.

Bone, *Annals of Internal Medicine*, vol. 115, No. 6, pp. 457–469, 1991.

Natanson et al, *NIH Conference, Annals of Internal Medicine*, vol. 120, No. 9, pp. 771–783, 1994.

Glausen et al., *The Lancet*, vol. 338, pp. 732–736, 1991.

Marijke et al, *Blood*, vol. 85, No. 12, pp. 3437–3443, Jun. 15, 1995.

Marijke et al, *The Journal of Infectious Diseases*, vol. 172, pp. 144–151, 1995.

Yao et al, *Annals of Surgery*, vol. 221, No. 4, pp. 398–405, 1995.

1

THERAPEUTIC USES OF BPI PROTEIN PRODUCTS IN HUMANS WITH HEMMORHAGE DUE TO TRAUMA

This is a Continuation of U.S. application Ser. No. 08/652,292, filed May 23, 1996, now abandoned.

BACKGROUND OF THE INVENTION

The present invention relates generally to methods and materials for treating humans suffering from hemorrhage due to trauma, by administration of bactericidal/permeability-increasing (BPI) protein products.

Acute traumatic hemorrhage, generally requiring immediate surgical intervention, is a major contributor to morbidity and mortality in the U.S. [Bickell et al., New Eng. J. Med., 331:1105–1109 (1994), Tran et al., Surgery, 114:21–30 (1993).] In 1982, there were approximately 165,000 deaths in the U.S. due to trauma, with at least two additional cases of permanent disability for each death. About 50% of these traumatic deaths occur immediately, due to direct injury to the central nervous system, heart, or one of the major blood vessels. Additional early deaths, approximately 30%, occur within several hours after injury, usually due to uncontrolled hemorrhage. The remaining 20% of deaths are so-called "late deaths", occuring during days to weeks after injury, due to complications from the traumatic hemorrhage that include infection or multiple organ system failure (MOSF) in about 80% of the cases. [Trunkey, Sci. Am., 249:28–35 (1983), Trunkey, New Eng. J. Med., 324:1259–1263 (1991).]

Among those patients who survive the immediate resuscitative and surgical interventions, approximately 10–40% suffer from a variety of morbidities, including, for example, systemic inflammation, wound infections, pneumonia, sepsis, respiratory failure, renal failure, coagulopathy, and pancreatitis. Hemorrhage and transfusion requirements may be specifically linked to increased risk of postoperative infection, respiratory complications, and multiorgan system failure [Agarwal et al., Arch. Surg., 128:171–177 (1993), Duke et al., Arch. Surg., 128:1125–1132 (1993), Tran et al., supra].

The causes of these complications from traumatic hemorrhage are multifactorial and interrelated. Many morbidities may be related to systemic inflammation following injury. It has also been hypothesized that physical trauma to tissue, direct tissue hypoperfusion, and translocation of endogenous bacteria and absorption of endotoxin from the gut lumen (due to hypoperfusion and/or other injury to the gastrointestinal tract) may play a role in the pathogenesis of these complications. The relevance of these proposed factors in the pathophysiology of the morbidities and late deaths associated with acute hemorrhagic shock in humans, however, is not clear.

Although acute traumatic hemorrhage is one potential cause of hypovolemic shock (i.e., shock due to decreased intravascular volume), there are numerous other potential causes, such as internal bleeding, e.g., gastrointestinal hemorrhage, intraperitoneal or retroperitoneal hemorrhage, hemorrhage into the femoral compartment, intrathoracic hemorrhage, aortic dissection and ruptured aortic aneurysm; excessive fluid loss due to, e.g., severe vomiting due to an intestinal or pyloric obstruction, severe diarrhea, sweating, dehydration, excessive urination (due to diabetes mellitus, diabetes insipidus, excessive diuretics, or the diuretic phase of acute renal failure) peritonitis, pancreatitis, planchnic ischemia, gangrene, bums; vasodilation due to, e.g., nervous system damage, anesthesia, ganglionic and adrenergic blockers, barbiturate overdose, poisons; and metabolic, toxic, or humoral vasodilatation, such as acute adrenal insufficiency, or an anaphylactic reaction. Other causes of shock unrelated to circulatory volume loss include cardiogenic shock (e.g., acute myocardial infarction, cardiac tamponade) and obstructive shock (e.g., acute pulmonary embolism). [See, e.g., Manual of Medical Therapeutics, 28th ed., Ewald et al., eds., Little, Brown and Company, Boston (1995); Cecil's Textbook of Medicine, 17th ed., Wyngaarden et al., eds., W. B. Saunders Co., Philadelphia (1985).]

As outlined below in Table I below, a normal individual can rapidly lose up to 20 per cent of the blood volume without any signs or symptoms. Limited signs of cardiovascular distress appear with losses up to 30 per cent of the blood volume, but signs and symptoms of hypovolemic shock generally appear when the blood loss exceeds 30 to 40 per cent of the blood volume.

TABLE I

| Percentage of Blood Volume Lost | Amount Lost (ml) | Clinical Manifestations |
|---|---|---|
| 10–20% | 500–1000 | Usually none, perhaps mild postural hypotension an tachycardia in response to exercise; vasovagal syncope may occur in 5% of cases |
| 20–30% | 1000–1500 | Few changes supine; light-headedness and hypotension commonly occur when upright; marked tachycardia in response to exertion |
| 30–40% | 1500–2000 | Blood pressure, cardiac output, central venous pressure, and urine volume are reduced even when supine; thirst, shortness of breath, clammy skin, sweating, clouding of consciousness and rapid, thready pulse may be noted |
| 40–50% | 2000–2500 | Severe shock, often resulting in death |

The patient is frequently oliguric, with a urinary output of less than 20 mL per hour. Frequently, the physical findings follow a progressive pattern as shock evolves from the early compensated phase to the advanced stages. In Stage I, physiologic compensatory mechanisms, such as increased cardiac output or elevated systemic vascular resistance, are effective and minimal clinical symptoms and signs are observed. In Stage II these mechanisms cannot effectively compensate for the blood volume loss, and the patient may exhibit hypotension, tachycardia, and hyperventilation. The decreased perfusion of vital organs can result in an altered mental state ranging from agitation to stupor to coma, reduced urinary output, and myocardial ischemia (in patients with coronary artery disease). The external appearance of the patient also reflects excessive sympathetic discharge, with cyanosis, coldness, and clamminess of the skin. In Stage III, which may be irreversible, the excessive and prolonged reduction of tissue perfusion leads to significant alterations in cellular membrane function, aggregation of blood corpuscles, and "sludging" in the capillaries. The vasoconstriction which has taken place in the less vital organs in order to maintain blood pressure in now excessive and has reduced flow to such an extent that cellular damage occurs.

Following traumatic hemorrhage, conventional therapy is directed at stopping the hemorrhage, combating shock, and restoring the blood volume. Prompt fluid resuscitation is preferably given through large-bore catheters placed in large peripheral veins. The pneumatic antishock garment, with sequential inflation of legs and abdominal compartments to 15–40 mm Hg, may temporily stabilize patients by increasing peripheral systemic vascular resistance. Restoration of the blood volume may be achieved by intravenous infusion of electrolyte solutions; colloid solutions of plasma protein, albumin, or dextran; or fresh whole blood. In the emergency situation, electrolyte solutions, albumin, or dextran are preferred over fresh whole blood because of the large amounts of fluid required, the possible delay in transfusion if typing and cross-matching are performed, and the possibility of allergic transfusion reactions. When shock is due to hemorrhage, packed red blood cells should be given as soon as feasible. When hemorrhage is massive, type-specific unmatched blood can be given safely. Rarely, type O blood may be needed.

Rapid infusion of Ringer's lactated or normal saline solution is the most widely used fluid therapy following hemorrhage. An initial infusion of two to three times the volume of the estimated blood loss is administered. Because these solutions are rapidly distributed throughout the intravascular and extravascular compartments, they must be supplemented with colloid solutions. When large volumes of electrolyte solutions are infused, patients often develop peripheral edema and elderly patients may develop pulmonary edema.

The colloidal preparations in wide use include a 6 per cent solution of high molecular weight dextran (dextran 70), a 10 per cent solution of low molecular weight dextran (dextran 40), and a 5 per cent solution of albumin in normal saline. Infusions of dextran 70 produce an initial volume effect slightly greater than the amount infused. Dextran 70 is slowly cleared over one to two days, allowing time for normal physiologic mechanisms to replace the volume lost. Dextran 40 has the advantage of an initial volume effect of nearly twice the amount infused. The lower molecular weight material is more rapidly cleared, however, and the volume-expanding effect is dissipated by 24 hours, before normal volume replacement mechanisms are maximal. Acute renal failure has occurred in a few patients receiving dextran 40. With either dextran solution, volumes in excess of one liter may interfere with platelet adhesiveness and the normal coagulation cascade. A solution of 5 per cent albumin in normal saline has the advantage of producing a known volume effect in the hypovolemic patient, but this preparation is relatively costly and time-consuming to prepare. A hypertonic albumin preparation containing 120 mEq of sodium lactate, 120 mEq of sodium chloride, and 12.5 grams of albumin per liter provides a predictable volume effect and minimizes interstitial fluid leakage. Use of hypertonic solutions requires careful monitoring of arterial and central venous pressures to avoid fluid overload. Coexisting problems such as congestive heart failure, valvular heart disease, myocardial ischemia, or renal insufficiency must be carefully monitored, and invasive hemodynamic monitoring must be considered during acute management. Associated coagulopathy and electrolyte imbalance must also be corrected.

BPI is a protein isolated from the granules of mammalian polymorphonuclear leukocytes (PMNs or neutrophils), which are blood cells essential in the defense against invading microorganisms. Human BPI protein has been isolated from PMNs by acid extraction combined with either ion exchange chromatography [Elsbach, *J. Biol. Chem.*, 254:11000 (1979)] or *E. coli* affinity chromatography [Weiss, et al., *Blood*, 69:652 (1987)]. BPI obtained in such a manner is referred to herein as natural BPI and has been shown to have potent bactericidal activity against a broad spectrum of gram-negative bacteria. The molecular weight of human BPI is approximately 55,000 daltons (55 kD). The amino acid sequence of the entire human BPI protein and the nucleic acid sequence of DNA encoding the protein have been reported in Figure 1 of Gray et al., *J. Biol. Chem.*, 264:9505 (1989), incorporated herein by reference. The Gray et al. amino acid sequence is set out in SEQ ID NO: 1 hereto. U.S. Pat. No. 5,198,541 discloses recombinant genes encoding and methods for expression of BPI proteins, including BPI holoprotein and fragments of BPI.

BPI is a strongly cationic protein. The N-terminal half of BPI accounts for the high net positive charge; the C-terminal half of the molecule has a net charge of −3. [Elsbach and Weiss (1981), supra.] A proteolytic N-terminal fragment of BPI having a molecular weight of about 25 kD possesses essentially all the anti-bacterial efficacy of the naturally-derived 55 kD human BPI holoprotein. [Ooi et al., *J. Bio. Chem.*, 262: 14891–14894 (1987)]. In contrast to the N-terminal portion, the C-terminal region of the isolated human BPI protein displays only slightly detectable anti-bacterial activity against gram-negative organisms. [Ooi et al., *J. Exp. Med.*, 174:649 (1991).] An N-terminal BPI fragment of approximately 23 kD, referred to as "rBPI$_{23}$," has been produced by recombinant means and also retains anti-bacterial activity against gram-negative organisms. Gazzano-Santoro et al., *Infect. Immun.* 60:4754–4761 (1992).

The bactericidal effect of BPI has been reported to be highly specific to gram-negative species, e.g., in Elsbach and Weiss, *Inflammation: Basic Principles and Clinical Correlates*, eds. Gallin et al., Chapter 30, Raven Press, Ltd. (1992). The precise mechanism by which BPI kills gram-negative bacteria is not yet completely elucidated, but it is believed that BPI must first bind to the surface of the bacteria through electrostatic and hydrophobic interactions between the cationic BPI protein and negatively charged sites on LPS. In susceptible gram-negative bacteria, BPI binding is thought to disrupt LPS structure, leading to activation of bacterial enzymes that degrade phospholipids and peptidoglycans, altering the permeability of the cell's outer membrane, and initiating events that ultimately lead to cell death. [Elsbach and Weiss (1992), supra]. LPS has been referred to as "endotoxin" because of the potent inflammatory response that it stimulates, i.e., the release of mediators by host inflammatory cells which may ultimately result in irreversible endotoxic shock. BPI binds to lipid A, reported to be the most toxic and most biologically active component of LPS.

BPI protein has never been used previously for the treatment of humans suffering from hemorrhage due to trauma or the shock associated with traumatic blood loss (i.e., hypovolemic shock). Bahrami et al., presentation at Vienna International Endotoxin Society Meeting, August, 1992, report the administration of BPI protein to rats subjected to hemorrhage. Yao et al., *Ann. Surg.*, 221:398–405 (1995), report the administration of rBPI$_{21}$ (described infra) to rats subjected to prolonged hemorrhagic insult for 180 minutes followed by resuscitation. U.S. Pat. Nos. 5,171,739, 5,089,724 and 5,234,912 report the use of BPI in various in vitro and in vivo animal model studies asserted to be correlated to methods of treating endotoxin-related diseases, including endotoxin-related shock. In co-owned, co-pending U.S. application Ser. Nos. 08/378,228, filed Jan. 24, 1995, 08/291,112, filed Aug. 16, 1994, and 08/188,221, filed Jan. 24, 1994, incorporated herein by reference, the administration of BPI protein product to humans with endotoxin in circulation was described. [See also, von der Möhlen et al., *J. Infect. Dis.* 172:144–151 (1995); von der Möhlen et al.,

*Blood* 85:3437–3443 (1995); de Winter et al., *J. Inflam.* 45:193–206 (1995)]. In co-owned, co-pending U.S. application Ser. No. 08/644,287, filed May 10, 1995 the administration of BPI protein product to humans suffering from severe meningococcemia was described.

In spite of treatment with antibiotics and state-of-the-art medical intensive care therapy, human mortality and morbidities associated with hemorrhage due to trauma remain significant and unresolved by current therapies. New therapeutic methods are needed that could reduce or ameliorate the adverse events and improve the clinical outcome of such patients.

SUMMARY OF THE INVENTION

The present invention provides novel methods for treating humans suffering from hemorrhage due to trauma, involving the administration of BPI protein products to provide clinically verifiable alleviation of the adverse effects of, or complications associated with, this disease state, including mortality and complications or morbidities.

According to the invention, BPI protein products such as $rBPI_{21}$ are administered to humans suffering from acute traumatic hemorrhage in amounts sufficient to reduce or prevent mortality and/or to reduce the incidence (i.e., occurrence) or severity of complications or morbidities, including infection (e.g., surgical site infection) or organ dysfunction (e.g., disseminated intravascular coagulation, acute respiratory distress syndrome, acute renal failure, or hepatobiliary dysfunction).

Numerous additional aspects and advantages of the invention will become apparent to those skilled in the art upon consideration of the following detailed description of the invention which describes presently preferred embodiments thereof.

DETAILED DESCRIPTION

Acute hemorrhage due to trauma is a life-threatening condition with significant mortality and morbidities despite state-of-the-art medical intensive care. The administration of BPI protein products to humans suffering from acute traumatic hemorrhage is expected to effectively decrease mortality and reduce the incidence (i.e., occurrence) or severity of complications or morbidities associated with or resulting from hemorrhage due to trauma. Complications include infection (e.g., in surgical sites, wounds, organs, anatomical spaces, the bloodstream, the urinary tract, or pneumonia) or organ dysfunction (e.g., disseminated intravascular coagulation, acute respiratory distress syndrome, acute renal failure, or hepatobiliary dysfunction), and may include serious complications. These unexpected effects on the mortality and complications associated with and resulting from hemorrhage due to trauma indicate that BPI protein products effectively interfere with or block a number of the multiple poorly-understood pathophysiologic processes that have led to poor outcomes in this condition.

BPI protein products are expected to provide beneficial effects for patients suffering from hemorrhage due to trauma, such as reduced injury severity score, reduced length of time on ventilatory support and inotropic (vasoactive) therapy, reduced duration or severity of associated coagulopathy, reduced stay in the ICU, reduced stay in the hospital overall, and reduced incidence and duration of complications such as coagulopathy, respiratory failure, renal failure, hepatic failure, coma or altered mental state, adrenal cortical necrosis, and severe infection, including in wounds, organs, anatomical spaces, the bloodstream, the urinary tract, or pneumonia.

Therapeutic compositions comprising BPI protein product may be administered systemically or topically. Systemic routes of administration include oral, intravenous, intramuscular or subcutaneous injection (including into a depot for long-term release), intraocular and retrobulbar, intrathecal, intraperitoneal (e.g. by intraperitoneal lavage), intrapulmonary using aerosolized or nebulized drug, or transdermal. The preferred route is intravenous administration. When given parenterally, BPI protein product compositions are generally injected in doses ranging from 1 µg/kg to 100 mg/kg per day, preferably at doses ranging from 0.1 mg/kg to 20 mg/kg per day, more preferably at doses ranging from 1 to 20 mg/kg/day and most preferably at doses ranging from 2 to 10 mg/kg/day. The treatment may continue by continuous infusion or intermittent injection or infusion, at the same, reduced or increased dose per day for, e.g., 1 to 3 days, and additionally as determined by the treating physician. BPI protein products are preferably administered intravenously by an initial bolus followed by a continuous infusion. One preferred regimen is a 1 to 20 mg/kg intravenous bolus of BPI protein product followed by intravenous infusion at a dose of 1 to 20 mg/kg/day, continuing for up to one week. Another preferred dosing regimen is a 2 to 10 mg/kg initial bolus followed by intravenous infusion at a dose of 2 to 10 mg/kg/day, continuing for up to 72 hours. Presently preferred is a continuous intravenous infusion of BPI protein product at a dose of 8 mg/kg over 48 hours. Topical routes include administration in the form of salves, ophthalmic drops, ear drops, irrigation fluids (for, e.g., irrigation of wounds) or medicated shampoos. For example, for topical administration in drop form, about 10 to 200 µL of a BPI protein product composition may be applied one or more times per day as determined by the treating physician. Those skilled in the art can readily optimize effective dosages and administration regimens for therapeutic compositions comprising BPI protein product, as determined by good medical practice and the clinical condition of the individual patient.

As used herein, "BPI protein product" includes naturally and recombinantly produced BPI protein; natural, synthetic, and recombinant biologically active polypeptide fragments of BPI protein; biologically active polypeptide variants of BPI protein or fragments thereof, including hybrid fusion proteins and dimers; biologically active polypeptide analogs of BPI protein or fragments or variants thereof, including cysteine-substituted analogs; and BPI-derived peptides. The BPI protein products administered according to this invention may be generated and/or isolated by any means known in the art. U.S. Pat. No. 5,198,541, the disclosure of which is incorporated herein by reference, discloses recombinant genes encoding and methods for expression of BPI proteins including recombinant BPI holoprotein, referred to as $rBPI_{50}$ (or rBPI) and recombinant fragments of BPI. Co-owned, copending U.S. patent application Ser. No. 07/885,501 and a continuation-in-part thereof, U.S. patent application Ser. No. 08/072,063 filed May 19, 1993 and corresponding PCT Application No. 93/04752 filed May 19, 1993, which are all incorporated herein by reference, disclose novel methods for the purification of recombinant BPI protein products expressed in and secreted from genetically transformed mammalian host cells in culture and discloses how one may produce large quantities of recombinant BPI products suitable for incorporation into stable, homogeneous pharmaceutical preparations.

Biologically active fragments of BPI (BPI fragments) include biologically active molecules that have the same or similar amino acid sequence as a natural human BPI holoprotein, except that the fragment molecule lacks amino-terminal amino acids, internal amino acids, and/or carboxy-terminal amino acids of the holoprotein. Nonlimiting examples of such fragments include a N-terminal fragment of natural human BPI of approximately 25 kD, described in Ooi et al., *J. Exp. Med.*, 174:649 (1991), and the recombinant expression product of DNA encoding N-terminal amino acids from 1 to about 193 or 199 of natural human BPI, described in Gazzano-Santoro et al., *Infect. Immun.* 60:4754–4761 (1992), and referred to as $rBPI_{23}$. In that publication, an expression vector was used as a source of DNA encoding a recombinant expression product ($rBPI_{23}$) having the 31-residue signal sequence and the first 199 amino acids of the N-terminus of the mature human BPI, as set out in Figure 1 of Gray et al., supra, except that valine at position 151 is specified by GTG rather than GTC and residue 185 is glutamic acid (specified by GAG) rather than lysine (specified by AAG). Recombinant holoprotein ($rBPI_{50}$) has also been produced having the sequence (SEQ ID NOS: 1 and 2) set out in FIGURE 1 of Gray et al., supra, with the exceptions noted for $rBPI_{23}$ and with the exception that residue 417 is alanine (specified by GCT) rather than valine (specified by GTT). Other examples include dimeric forms of BPI fragments, as described in co-owned and co-pending U.S. patent application Ser. No. 08/212,132, filed Mar. 11, 1994, and corresponding PCT Application No. PCT/US95/03125, the disclosures of which are incorporated herein by reference. Preferred dimeric products include dimeric BPI protein products wherein the monomers are amino-terminal BPI fragments having the N-terminal residues from about 1 to 175 to about 1 to 199 of BPI holoprotein. A particularly preferred dimeric product is the dimeric form of the BPI fragment having N-terminal residues 1 through 193, designated $rBPI_{42}$ dimer.

Biologically active variants of BPI (BPI variants) include but are not limited to recombinant hybrid fusion proteins, comprising BPI holoprotein or biologically active fragment thereof and at least a portion of at least one other polypeptide, and dimeric forms of BPI variants. Examples of such hybrid fusion proteins and dimeric forms are described by Theofan et al. in co-owned, copending U.S. patent application Ser. No. 07/885,911, and a continuation-in-part application thereof, U.S. patent application Ser. No. 08/064,693 filed May 19, 1993 and corresponding PCT Application No. US93/04754 filed May 19, 1993, which are all incorporated herein by reference and include hybrid fusion proteins comprising, at the amino-terminal end, a BPI protein or a biologically active fragment thereof and, at the carboxy-terminal end, at least one constant domain of an immunoglobulin heavy chain or allelic variant thereof. Similarly configured hybrid fusion proteins involving part or all Lipopolysaccharide Binding Protein (LBP) are also contemplated for use in the present invention.

Biologically active analogs of BPI (BPI analogs) include but are not limited to BPI protein products wherein one or more amino acid residues have been replaced by a different amino acid. For example, co-owned, copending U.S. patent application Ser. No. 08/013,801 filed Feb. 2, 1993 and corresponding PCT Application No. US94/01235 filed Feb. 2, 1994, the disclosures of which are incorporated herein by reference, discloses polypeptide analogs of BPI and BPI fragments wherein a cysteine residue is replaced by a different amino acid. A preferred BPI protein product described by this application is the expression product of DNA encoding from amino acid 1 to approximately 193 or 199 of the N-terminal amino acids of BPI holoprotein, but wherein the cysteine at residue number 132 is substituted with alanine and is designated $rBPI_{21}\Delta cys$ or $rBPI_{21}$. Other examples include dimeric forms of BPI analogs; e.g. co-owned and co-pending U.S. patent application Ser. No. 08/212,132 filed Mar. 11, 1994, and corresponding PCT Application No. PCT/US95/03125, the disclosures of which are incorporated herein by reference.

Other BPI protein products useful according to the methods of the invention are peptides derived from or based on BPI produced by recombinant or synthetic means (BPI-derived peptides), such as those described in co-owned and co-pending U.S. patent application Ser. No. 08/504,841 filed Jul. 20, 1995 and in co-owned and copending PCT Application No. PCT/US94/10427 filed Sep. 15, 1994, which corresponds to U.S. patent application Ser. No. 08/306,473 filed Sep. 15, 1994, and PCT Application No. US94/02465 filed Mar. 11, 1994, which corresponds to U.S. patent application Ser. No. 08/209,762, filed Mar. 11, 1994, which is a continuation-in-part of U.S. patent application Ser. No. 08/183,222, filed Jan. 14, 1994, which is a continuation-in-part of U.S. patent application Ser. No. 08/093,202 filed Jul. 15, 1993 (for which the corresponding international application is PCT Application No. US94/02401 filed Mar. 11, 1994), which is a continuation-in-part of U.S. patent application Ser. No. 08/030,644 filed Mar. 12, 1993, the disclosures of all of which are incorporated herein by reference.

Presently preferred BPI protein products include recombinantly-produced N-terminal fragments of BPI, especially those having a molecular weight of approximately between 21 to 25 kD such as $rBPI_{23}$ or $rBPI_{21}$, or dimeric forms of these N-terminal fragments (e.g., $rBPI_{42}$ dimer). Additionally, preferred BPI protein products include $rBPI_{50}$ and BPI-derived peptides. Particularly preferred is $rBPI_{21}$.

The administration of BPI protein products is preferably accomplished with a pharmaceutical composition comprising a BPI protein product and a pharmaceutically acceptable diluent, adjuvant, or carrier. The BPI protein product may be administered without or in conjunction with known surfactants, other chemotherapeutic agents or additional known anti-microbial agents. One pharmaceutical composition containing BPI protein products (e.g., $rBPI_{50}$, $rBPI_{23}$) comprises the BPI protein product at a concentration of 1 mg/ml in citrate buffered saline (5 or 20 mM citrate, 150 mM NaCl, pH 5.0) comprising 0.1% by weight of poloxamer 188 (Pluronic F-68, BASF Wyandotte, Parsippany, N.J.) and 0.002% by weight of polysorbate 80 (Tween 80, ICI Americas Inc., Wilmington, Del.). Another pharmaceutical composition containing BPI protein products (e.g., $rBPI_{21}$) comprises the BPI protein product at a concentration of 2 mg/mL in 5 mM citrate, 150 mM NaCl, 0.2% poloxamer 188 and 0.002% polysorbate 80. Such combinations are described in co-owned, co-pending PCT Application No. US94/01239 filed Feb. 2, 1994, which corresponds to U.S. patent application Ser. No. 08/190,869 filed Feb. 2, 1994 and U.S. patent application Ser. No. 08/012,360 filed Feb. 2, 1993, the disclosures of all of which are incorporated herein by reference.

Other aspects and advantages of the present invention will be understood upon consideration of the following illustrative examples. Example 1 addresses the effect of BPI protein product administration in humans on the mortality and complications associated with hemorrhage due to trauma.

EXAMPLE 1

Clinical Study Protocol—Therapeutic Effects of BPI Protein Product

A human clinical study was designed to examine the effect of an exemplary BPI protein product, $rBPI_{21}$, in the treatment of patients with acute hemorrhage due to trauma. Thus, a multicenter, randomized, double-blind, placebo-controlled trial was implemented comparing placebo treatment and $rBPI_{21}$ treatment given over 48 hours in patients with acute hemorrhage due to trauma. Approximately 400 patients admitted to the emergency department with acute hemorrhage due to trauma and requiring transfusion of at least two units of blood are randomized in a 1:1 ratio for treatment with either $rBPI_{21}$ or placebo. In addition to standard therapy, each patient receives by continuous intravenous infusion either $rBPI_{21}$ at 8 mg/kg over 48 hours (4 mg/kg/day×2 days) or the equivalent volume of placebo. In most instances the weight of the patient in kilograms is determined as a best estimate.

Efficacy is monitored from Day 1 to Day 15 by following patients for development of complications, such as impaired organ function and infection, and for survival. Safety is monitored by pre-treatment and serial post-treatment testing of chemistries and hematology parameters, as well as daily assessments for adverse events through Day 15. A final survival assessment occurs on Day 29. Immune response to and pharmacokinetics of $rBPI_{21}$ are measured at selected study sites by drawing blood to assay for $rBPI_{21}$ at appropriate time points.

Patients brought to the hospital with acute hemorrhage due to trauma are selected for enrollment in the study if they meet the following inclusion and exclusion criteria. Inclusion criteria are: (1) age 18 (or age of consent) to 75 years, inclusive; (2) patient suffering from acute hemorrhage secondary to trauma; (3) study drug given within 6 hours of occurrence of the traumatic event (if precise time of event was unknown best estimate was provided); (4) patient requires and has begun to receive a second unit of packed red blood cells; and (5) patient provides verbal informed consent or next of kin provides written informed consent. Exclusion criteria are: (1) a triage Revised Trauma Score (RTS, scale 0–12) less than 2.0 upon admission to the Emergency Department, see Table II below [Champion et al., *Crit. Care Med.*, 9(9):672–676 (1981); Greenfield et al., Chapter 10, in *Surgery Scientific Principles and Practices*, J. B. Lippincott Co., Philadelphia, pp. 252–255 (1993)]; (2) severe head trauma (Glasgow Coma Score≦5), see Table III below [Teasdale et al., *Lancet*, 1: 81 (1974)]; (3) isolated cranial injury; (4) spinal injury with paralysis; (5) burn injuries with at least 20% body surface area with second degree burns; (6) known positive HIV (test not mandatory at entry); (7) known pre-existing renal disease (creatinine>2.0); (8) known pre-existing cardiac disease (NY Heart Association class greater than III, see Table IV below [Braunwald, in Braunwald et al., *Heart Disease, The Textbook of Cardiovascular Medicine*, 3rd ed., W. B. Saunders Company, Philadelphia, Pa., page 12 (1988); *J. Am. Med. Ass'n*, 249:539–544 (1988)]); (9) known pre-existing primary or metastatic malignancy in visceral organs; (10) arterial pH (at initial evaluation)<6.8 or base deficit>15 (if measured); (11) known current steroid therapy (>10 mg prednisone/day for>one month); (12) known pre-existing cirrhosis or active hepatitis; (13) pregnancy or lactation; (14) participation in other investigational drug studies (including investigational blood products) within previous 30 days; (15) weight (estimated) greater than 120 kg; and (16) a "do not resuscitate" (DNR) or equivalent order.

TABLE II

Triage Revised Trauma Score*

| ASSESSMENT | METHOD | CODING |
|---|---|---|
| 1. Respiratory Rate (RR) | Count respiratory rate in 15 sec and multiply by 4 | 10–29 = 4<br>>29 = 3<br>6–9 = 2<br>1–5 = 1<br>0 = 0 |
| 2. Systolic Blood Pressure (SBP) | Measure systolic cuff pressure in either arm by auscultation or palpation | >89 = 4<br>76–89 = 3<br>50–75 = 2<br>1–49 = 1<br>0 = 0 |
| 3. Glasgow Coma Score (GCS) | Calculate according to Table III below | Convert GCS to the Following Code:<br>13–15 = 4<br>9–12 = 3<br>6–8 = 2<br>4–5 = 1<br><4 = 0 |

*The triage revised trauma score is the sum of the codes for RR, SBP and GCS (range 0–12).

TABLE III

| | Glasgow Coma Scale* |
|---|---|
| Eye Opening | |
| Spontaneous | 4 |
| Response to sound | 3 |
| Response to pain | 2 |
| Never | 1 |
| Motor Response | |
| Obey commands | 6 |
| Localized pain | 5 |
| Normal flexion: (withdrawal) | 4 |
| Abnormal flexion (Decorticate) | 3 |
| No response | 1 |
| Verbal Response | |
| Oriented | 5 |
| Confused conversation | 4 |
| Inappropriate words | 3 |
| Incomprehensible sounds | 2 |
| None | 1 |

*Scores range from 3 to 15

TABLE IV

Modified New York Heart Association Functional Classification

| Class I. | Patients with cardiac disease but with no limitation of physical activity. Ordinary physical activity causes no undue dyspnea, anginal pain, fatigue, or palpitation. |
|---|---|
| Class IIS. | Patients with slight limitation of physical activity. They are comfortable at rest and with moderate exertion. They experience symptoms only with the more strenuous grades of ordinary activity. |
| Class IIM. | Patients with moderate limitation of physical ability. They are comfortable at rest and with mild exertion. They experience symptoms with moderate grades of ordinary activity. |
| Class III. | Patients with marked limitation of physical activity. They are comfortable at rest but experience symptoms even with the milder forms of ordinary activity. |
| Class IV. | Patients with inability to carry on any physical activity without discomfort. Symptoms of cardiac insufficiency |

TABLE IV-continued

Modified New York Heart Association
Functional Classification or of the anginal syndrome may be present, even at rest, and are intensified by activity.

The following are recorded for all patients randomized to treatment: (1) date and estimated time of incident, and date and time of admission to the Emergency Department; (2) for patients randomized and not treated, the reason for not treating; (3) from arrival at hospital until approximately 48 hours post-operatively, date, time, volume, and location that patient receives blood, blood products, and fluids such as packed red blood cells, whole blood, autotransfusion, platelets, fresh frozen plasma, crystalloid, or colloid, at locations such as Emergency Department, Operating Room, Post-anesthesia Care Unit, or Surgical Intensive Care Unit; however, if the patient does not undergo surgery, the above items that are applicable are collected during study days 1, 2, and 3; (4) date and time the second unit of blood is administered (should precede surgery, to assure that hemorrhage is due to trauma, not surgery), and date and start and stop times of anesthesia; (5) date and start and stop times of surgery, estimated blood loss in operating room, and date and time in post-anesthesia care unit; (6) date and time study drug infusion begins and ends, volume infused, and reasons for temporary or permanent discontinuation; if applicable, and if discontinued, quantity infused; (7) directed medical history (including extent and nature of injuries, intercurrent diseases, conditions contributing to bleeding, etc.), demographic and directed physical exam information, such as gender, age, weight (estimated or measured), height (estimated or measured), vital signs, physical signs of injury; (8) results of the pregnancy test performed during screening for eligibility of appropriate female patients (refers to all women of child bearing potential, i.e., all women who are not either surgically sterile or documented to be post-menopausal); and (9) results of the triage RTS performed during screening for eligibility (including actual measurements).

After transfusion of the second unit of blood is initiated, the investigator administers an unknown test drug from kits in numbered consecutive order. Each kit contains either $rBPI_{21}$ or placebo. The $rBPI_{21}$ is supplied as a clear, colorless, sterile non-pyrogenic solution in 10 mL single use glass vials at a concentration of 2 mg/mL, in 5 mM sodium citrate/0.15M sodium chloride buffer, pH 5.0 with 0.2% poloxamer 188 and 0.002% polysorbate 80, containing no preservative. The $rBPI_{21}$ is stored refrigerated at 2°–8° C. at all times prior to administration. The placebo is supplied as a clear, colorless sterile non-pyrogenic solution in 10 mL single use glass vials. It is composed of 0.2 mg/mL human serum albumin in 5 mM sodium citrate/0.15M sodium chloride buffer, pH 5.0, containing no preservative. The placebo is stored refrigerated at 2°–8° C. at all times prior to administration. The kit assigned to each patient contains a sufficient number of vials of study medication for all doses for that patient. Each vial contains 10 mL of test article.

The study is administered to two groups ("active" $rBPI_{21}$ and placebo control) as outlined above. The study medication is brought to room temperature prior to infusion. Throughout the dosing procedure, good aseptic technique for intravenous administration is followed. The study medication is administered by intravenous infusion into a central or peripheral vein over 48 hours. The infusion bag/tubing administration set is completely changed after 24 hours. Suitability of intravenous access is determined by easy withdrawal of blood from the access, as well as easy infusion of intravenous fluids without infiltration. The study medication is the sole agent administered in the chosen port during the course of the infusion protocol. The venous access port is not heparinized, but is flushed as necessary with physiologic saline. Any sign of a reaction at a site of infusion is recorded on the patient's case record form and source document as an adverse experience.

All patients treated at selected study sites are assessed for: (1) blood levels of $rBPI_{21}$: blood for the assessment of the $rBPI_{21}$ level is drawn at the following times (at selected study sites only): prior to the start of the infusion (up to 60 minutes prior to the start of the infusion), the following times (hours) after the start of the infusion: 1, 4, 8, 12, 20, 24, 32, 36, 40, within 15 minutes prior to the completion of the 48 hour infusion, and the following times after completion of the infusion; 7 minutes (48:07), 15 minutes (48:15), 30 minutes (48:30), 1 hour (49:00), 3 hours (51:00), 6 hours (54:00), and 24 hours (72:00); (2) antibodies to $rBPI_{21}$: blood for assessment of antibodies to $rBPI_{21}$ is drawn at selected study sites at the following times: Day 1 prior to study drug infusion, and Days 15 and 29, if the patient is still in hospital or returns to clinic. Actual draw days may vary from Days 10–20 and Days 21–29; and (3) cytokines: blood for assessment of cytokines is drawn at selected study sites.

The following safety laboratory panels are assessed at Day 1 prior to test drug infusion, Day 3 (after end of infusion) and Day 8, however, if patient is discharged on or prior to Day 8, assessment is made prior to discharge if possible: (1) hematology panel: hemoglobin, hematocrit, erythrocyte count, leukocyte count and differential, and platelet count; (2) serum chemistry panel: sodium, potassium, chloride, calcium, phosphorous, blood urea nitrogen, creatinine, uric acid, glucose (fasting), CPK, cholesterol, albumin, total protein, AST (SGOT), ALT (SGPT), bilirubin (total), GGT, LDH, and alakaline phosphatase.

The following are recorded for all treated patients through Day 15 post-initiation of study drug infusion: (1) adverse events; (2) survival status including date and cause(s) of death (continued through Day 29); (3) dates in ICU; (4) dates in hospital; (5) dates on ventilator; (6) dates on dialysis or hemofiltration, specifying method; (7) concomitant medications, including daily amounts of blood transfused; (8) primary surgical procedures performed, for example, including re-operations but excluding procedures like placement of central lines, Swan-Ganz catheters, arterial lines; lumbar punctures, etc.; (9) injury severity score (ISS) based on diagnostic evaluations performed during current hospital stay; (10) daily assessment of infections and organ dysfunctions; (11) daily vital signs associated with and including daily maximum and daily minimum temperatures; and (12) inspection of infusion site used for study drug administration at least every eight hours, with observations documented in progress notes or the equivalent.

Organ dysfunctions were assessed as follows. The patient is considered to have disseminated intravascular coagulation when there are: (1) abnormally low values for platelets (or there is a >25% decrease from a previously documented value) and either an elevated prothrombin time or an elevated partial thromboplastin time and clinical evidence of bleeding, or (2) if obtained, a confirmatory test is positive (FDP>1:40 or D-Dimers>2.0). These abnormalities must occur in the absence of medically significant confounding factors such as liver failure, major hematoma, or anticoagulant therapy.

The patient is considered to have acute respiratory distress syndrome when: bilateral pulmonary infiltrates consistent with pulmonary edema are present, and $PaO_2/FiO_2<200$. These signs must occur in the absence of congestive heart failure or primary lung disease such as pulmonary embolus or pneumonia. The Pulmonary Artery Wedge Pressure (PAWP), when measured, must be <18 mm Hg.

The patient is considered to have acute renal failure when: (1) dialysis or hemofiltration is required (definition used for primary analysis), or (2) serum creatinine becomes abnormal with an increase of $\geq 2.0$ mg/dL in patient with documented normal baseline creatinine, or (3) serum creatinine is $\geq 3.0$ mg/dL in a patient not known to have renal insufficiency, but whose (pretrauma) baseline creatinine is unknown, or (4) serum creatinine is doubled from admission or pre-rBPI$_{21}$ treatment level in a patient with previous renal insufficiency. These findings must not be prerenal in nature (e.g. associated with dehydration or gastrointestinal bleeding) or due to rhabdomyolysis.

Post-surgical hepatobiliary dysfunction is evaluated only in patients without primary hepatic disease (e.g., hepatitis or cirrhosis), alcoholism, or biliary disease. The patient is considered to have hepatobiliary dysfunction when: the bilirubin exceeds 3.0 mg/dL, and either the alkaline phosphatase, gamma glutamyl transpeptidase (GGT), or alanine aminotransferase (ALT, or SGPT) exceeds twice the upper limit of normal. These findings must occur in the absence of confounding disease.

Patients are also evaluated for infections in wounds, surgical sites (both superficial and deep incisional sites), organs, anatomical spaces, the bloodstream, the urinary tract, or the respiratory tract (pneumonia).

Numerous modifications and variations of the above-described invention are expected to occur to those of skill in the art. Accordingly, only such limitations as appear in the appended claims should be placed thereon.

---

What is claimed is:

1. A method of treating a human suffering from hemorrhage due to trauma comprising the step of administering a therapeutically effective amount of a bactericidal/permeability-increasing (BPI) protein product to said human.

2. The method of claim 1 wherein the BPI protein product is an amino-terminal fragment of BPI protein having a molecular weight of about 21 kD to 25 kD.

3. The method of claim 1 wherein the BPI protein product is rBPI$_{23}$ or a dimeric form thereof.

4. The method of claim 1 wherein the BPI protein product is rBPI$_{21}$.

5. The method of claim 1 wherein the human suffering from hemorrhage due to trauma is additionally administered at least two units of packed red blood cells.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1813 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 31..1491

( i x ) FEATURE:
        ( A ) NAME/KEY: mat_peptide
        ( B ) LOCATION: 124..1491

( i x ) FEATURE:
        ( A ) NAME/KEY: misc_feature
        ( D ) OTHER INFORMATION: "rBPI"

( x i ) SEQUENCE DESCRIPTION: SEQ ID NO:1:

```
CAGGCCTTGA GGTTTTGGCA GCTCTGGAGG ATG AGA GAG AAC ATG GCC AGG GGC              54
                                Met Arg Glu Asn Met Ala Arg Gly
                                -31 -30                      -25

CCT TGC AAC GCG CCG AGA TGG GTG TCC CTG ATG GTG CTC GTC GCC ATA              102
Pro Cys Asn Ala Pro Arg Trp Val Ser Leu Met Val Leu Val Ala Ile
        -20                     -15                     -10

GGC ACC GCC GTG ACA GCG GCC GTC AAC CCT GGC GTC GTG GTC AGG ATC              150
Gly Thr Ala Val Thr Ala Ala Val Asn Pro Gly Val Val Val Arg Ile
        -5                       1              5

TCC CAG AAG GGC CTG GAC TAC GCC AGC CAG CAG GGG ACG GCC GCT CTG              198
Ser Gln Lys Gly Leu Asp Tyr Ala Ser Gln Gln Gly Thr Ala Ala Leu
 10              15                  20                      25

CAG AAG GAG CTG AAG AGG ATC AAG ATT CCT GAC TAC TCA GAC AGC TTT              246
Gln Lys Glu Leu Lys Arg Ile Lys Ile Pro Asp Tyr Ser Asp Ser Phe
                30                  35                  40

AAG ATC AAG CAT CTT GGG AAG GGG CAT TAT AGC TTC TAC AGC ATG GAC              294
Lys Ile Lys His Leu Gly Lys Gly His Tyr Ser Phe Tyr Ser Met Asp
            45                  50                  55
```

| | | | | | | | | | | | | | | | | |
|---|---|---|---|---|---|---|---|---|---|---|---|---|---|---|---|---|
| ATC | CGT | GAA | TTC | CAG | CTT | CCC | AGT | TCC | CAG | ATA | AGC | ATG | GTG | CCC | AAT | 342 |
| Ile | Arg | Glu | Phe | Gln | Leu | Pro | Ser | Ser | Gln | Ile | Ser | Met | Val | Pro | Asn | |
| | | 60 | | | | | 65 | | | | | 70 | | | | |
| GTG | GGC | CTT | AAG | TTC | TCC | ATC | AGC | AAC | GCC | AAT | ATC | AAG | ATC | AGC | GGG | 390 |
| Val | Gly | Leu | Lys | Phe | Ser | Ile | Ser | Asn | Ala | Asn | Ile | Lys | Ile | Ser | Gly | |
| | | 75 | | | | | 80 | | | | | 85 | | | | |
| AAA | TGG | AAG | GCA | CAA | AAG | AGA | TTC | TTA | AAA | ATG | AGC | GGC | AAT | TTT | GAC | 438 |
| Lys | Trp | Lys | Ala | Gln | Lys | Arg | Phe | Leu | Lys | Met | Ser | Gly | Asn | Phe | Asp | |
| 90 | | | | | 95 | | | | | 100 | | | | | 105 | |
| CTG | AGC | ATA | GAA | GGC | ATG | TCC | ATT | TCG | GCT | GAT | CTG | AAG | CTG | GGC | AGT | 486 |
| Leu | Ser | Ile | Glu | Gly | Met | Ser | Ile | Ser | Ala | Asp | Leu | Lys | Leu | Gly | Ser | |
| | | | | | 110 | | | | | 115 | | | | | 120 | |
| AAC | CCC | ACG | TCA | GGC | AAG | CCC | ACC | ATC | ACC | TGC | TCC | AGC | TGC | AGC | AGC | 534 |
| Asn | Pro | Thr | Ser | Gly | Lys | Pro | Thr | Ile | Thr | Cys | Ser | Ser | Cys | Ser | Ser | |
| | | | 125 | | | | | 130 | | | | | 135 | | | |
| CAC | ATC | AAC | AGT | GTC | CAC | GTG | CAC | ATC | TCA | AAG | AGC | AAA | GTC | GGG | TGG | 582 |
| His | Ile | Asn | Ser | Val | His | Val | His | Ile | Ser | Lys | Ser | Lys | Val | Gly | Trp | |
| | | 140 | | | | | 145 | | | | | 150 | | | | |
| CTG | ATC | CAA | CTC | TTC | CAC | AAA | AAA | ATT | GAG | TCT | GCG | CTT | CGA | AAC | AAG | 630 |
| Leu | Ile | Gln | Leu | Phe | His | Lys | Lys | Ile | Glu | Ser | Ala | Leu | Arg | Asn | Lys | |
| | | 155 | | | | | 160 | | | | | 165 | | | | |
| ATG | AAC | AGC | CAG | GTC | TGC | GAG | AAA | GTG | ACC | AAT | TCT | GTA | TCC | TCC | AAG | 678 |
| Met | Asn | Ser | Gln | Val | Cys | Glu | Lys | Val | Thr | Asn | Ser | Val | Ser | Ser | Lys | |
| 170 | | | | | 175 | | | | | 180 | | | | | 185 | |
| CTG | CAA | CCT | TAT | TTC | CAG | ACT | CTG | CCA | GTA | ATG | ACC | AAA | ATA | GAT | TCT | 726 |
| Leu | Gln | Pro | Tyr | Phe | Gln | Thr | Leu | Pro | Val | Met | Thr | Lys | Ile | Asp | Ser | |
| | | | | | 190 | | | | | 195 | | | | | 200 | |
| GTG | GCT | GGA | ATC | AAC | TAT | GGT | CTG | GTG | GCA | CCT | CCA | GCA | ACC | ACG | GCT | 774 |
| Val | Ala | Gly | Ile | Asn | Tyr | Gly | Leu | Val | Ala | Pro | Pro | Ala | Thr | Thr | Ala | |
| | | | 205 | | | | | 210 | | | | | 215 | | | |
| GAG | ACC | CTG | GAT | GTA | CAG | ATG | AAG | GGG | GAG | TTT | TAC | AGT | GAG | AAC | CAC | 822 |
| Glu | Thr | Leu | Asp | Val | Gln | Met | Lys | Gly | Glu | Phe | Tyr | Ser | Glu | Asn | His | |
| | | 220 | | | | | 225 | | | | | 230 | | | | |
| CAC | AAT | CCA | CCT | CCC | TTT | GCT | CCA | CCA | GTG | ATG | GAG | TTT | CCC | GCT | GCC | 870 |
| His | Asn | Pro | Pro | Pro | Phe | Ala | Pro | Pro | Val | Met | Glu | Phe | Pro | Ala | Ala | |
| | | 235 | | | | | 240 | | | | | 245 | | | | |
| CAT | GAC | CGC | ATG | GTA | TAC | CTG | GGC | CTC | TCA | GAC | TAC | TTC | TTC | AAC | ACA | 918 |
| His | Asp | Arg | Met | Val | Tyr | Leu | Gly | Leu | Ser | Asp | Tyr | Phe | Phe | Asn | Thr | |
| 250 | | | | | 255 | | | | | 260 | | | | | 265 | |
| GCC | GGG | CTT | GTA | TAC | CAA | GAG | GCT | GGG | GTC | TTG | AAG | ATG | ACC | CTT | AGA | 966 |
| Ala | Gly | Leu | Val | Tyr | Gln | Glu | Ala | Gly | Val | Leu | Lys | Met | Thr | Leu | Arg | |
| | | | | 270 | | | | | 275 | | | | | 280 | | |
| GAT | GAC | ATG | ATT | CCA | AAG | GAG | TCC | AAA | TTT | CGA | CTG | ACA | ACC | AAG | TTC | 1014 |
| Asp | Asp | Met | Ile | Pro | Lys | Glu | Ser | Lys | Phe | Arg | Leu | Thr | Thr | Lys | Phe | |
| | | | 285 | | | | | 290 | | | | | 295 | | | |
| TTT | GGA | ACC | TTC | CTA | CCT | GAG | GTG | GCC | AAG | AAG | TTT | CCC | AAC | ATG | AAG | 1062 |
| Phe | Gly | Thr | Phe | Leu | Pro | Glu | Val | Ala | Lys | Lys | Phe | Pro | Asn | Met | Lys | |
| | | 300 | | | | | 305 | | | | | 310 | | | | |
| ATA | CAG | ATC | CAT | GTC | TCA | GCC | TCC | ACC | CCG | CCA | CAC | CTG | TCT | GTG | CAG | 1110 |
| Ile | Gln | Ile | His | Val | Ser | Ala | Ser | Thr | Pro | Pro | His | Leu | Ser | Val | Gln | |
| | | 315 | | | | | 320 | | | | | 325 | | | | |
| CCC | ACC | GGC | CTT | ACC | TTC | TAC | CCT | GCC | GTG | GAT | GTC | CAG | GCC | TTT | GCC | 1158 |
| Pro | Thr | Gly | Leu | Thr | Phe | Tyr | Pro | Ala | Val | Asp | Val | Gln | Ala | Phe | Ala | |
| 330 | | | | | 335 | | | | | 340 | | | | | 345 | |
| GTC | CTC | CCC | AAC | TCC | TCC | CTG | GCT | TCC | CTC | TTC | CTG | ATT | GGC | ATG | CAC | 1206 |
| Val | Leu | Pro | Asn | Ser | Ser | Leu | Ala | Ser | Leu | Phe | Leu | Ile | Gly | Met | His | |
| | | | | 350 | | | | | 355 | | | | | 360 | | |
| ACA | ACT | GGT | TCC | ATG | GAG | GTC | AGC | GCC | GAG | TCC | AAC | AGG | CTT | GTT | GGA | 1254 |
| Thr | Thr | Gly | Ser | Met | Glu | Val | Ser | Ala | Glu | Ser | Asn | Arg | Leu | Val | Gly | |
| | | | 365 | | | | | 370 | | | | | 375 | | | |

```
GAG CTC AAG CTG GAT AGG CTG CTC CTG GAA CTG AAG CAC TCA AAT ATT      1302
Glu Leu Lys Leu Asp Arg Leu Leu Leu Glu Leu Lys His Ser Asn Ile
        380                 385                 390

GGC CCC TTC CCG GTT GAA TTG CTG CAG GAT ATC ATG AAC TAC ATT GTA      1350
Gly Pro Phe Pro Val Glu Leu Leu Gln Asp Ile Met Asn Tyr Ile Val
        395                 400                 405

CCC ATT CTT GTG CTG CCC AGG GTT AAC GAG AAA CTA CAG AAA GGC TTC      1398
Pro Ile Leu Val Leu Pro Arg Val Asn Glu Lys Leu Gln Lys Gly Phe
410                 415                 420                 425

CCT CTC CCG ACG CCG GCC AGA GTC CAG CTC TAC AAC GTA GTG CTT CAG      1446
Pro Leu Pro Thr Pro Ala Arg Val Gln Leu Tyr Asn Val Val Leu Gln
            430                 435                 440

CCT CAC CAG AAC TTC CTG CTG TTC GGT GCA GAC GTT GTC TAT AAA          1491
Pro His Gln Asn Phe Leu Leu Phe Gly Ala Asp Val Val Tyr Lys
                445                 450                 455

TGAAGGCACC AGGGGTGCCG GGGGCTGTCA GCCGCACCTG TTCCTGATGG GCTGTGGGGC    1551
ACCGGCTGCC TTTCCCCAGG GAATCCTCTC CAGATCTTAA CCAAGAGCCC CTTGCAAACT    1611
TCTTCGACTC AGATTCAGAA ATGATCTAAA CACGAGGAAA CATTATTCAT TGGAAAAGTG    1671
CATGGTGTGT ATTTTAGGGA TTATGAGCTT CTTTCAAGGG CTAAGGCTGC AGAGATATTT    1731
CCTCCAGGAA TCGTGTTTCA ATTGTAACCA AGAAATTTCC ATTTGTGCTT CATGAAAAAA    1791
AACTTCTGGT TTTTTCATG TG                                              1813
```

( 2 ) INFORMATION FOR SEQ ID NO:2:

( i ) SEQUENCE CHARACTERISTICS:
        ( A ) LENGTH: 487 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Arg Glu Asn Met Ala Arg Gly Pro Cys Asn Ala Pro Arg Trp Val
-31 -30              -25                 -20

Ser Leu Met Val Leu Val Ala Ile Gly Thr Ala Val Thr Ala Ala Val
-15             -10                  -5                       1

Asn Pro Gly Val Val Val Arg Ile Ser Gln Lys Gly Leu Asp Tyr Ala
                 5                  10                  15

Ser Gln Gln Gly Thr Ala Ala Leu Gln Lys Glu Leu Lys Arg Ile Lys
        20                  25                  30

Ile Pro Asp Tyr Ser Asp Ser Phe Lys Ile Lys His Leu Gly Lys Gly
        35                  40                  45

His Tyr Ser Phe Tyr Ser Met Asp Ile Arg Glu Phe Gln Leu Pro Ser
50              55                  60                      65

Ser Gln Ile Ser Met Val Pro Asn Val Gly Leu Lys Phe Ser Ile Ser
                70                  75                      80

Asn Ala Asn Ile Lys Ile Ser Gly Lys Trp Lys Ala Gln Lys Arg Phe
                85                  90                  95

Leu Lys Met Ser Gly Asn Phe Asp Leu Ser Ile Glu Gly Met Ser Ile
            100                 105                 110

Ser Ala Asp Leu Lys Leu Gly Ser Asn Pro Thr Ser Gly Lys Pro Thr
        115                 120                 125

Ile Thr Cys Ser Ser Cys Ser Ser His Ile Asn Ser Val His Val His
        130                 135                 140                 145

Ile Ser Lys Ser Lys Val Gly Trp Leu Ile Gln Leu Phe His Lys Lys
                150                 155                 160
```

| | | | | | | | | | | | | | | |
|---|---|---|---|---|---|---|---|---|---|---|---|---|---|---|
| Ile | Glu | Ser | Ala 165 | Leu | Arg | Asn | Lys | Met 170 | Asn | Ser | Gln | Val | Cys 175 | Glu | Lys |
| Val | Thr | Asn 180 | Ser | Val | Ser | Ser | Lys 185 | Leu | Gln | Pro | Tyr | Phe 190 | Gln | Thr | Leu |
| Pro | Val 195 | Met | Thr | Lys | Ile | Asp 200 | Ser | Val | Ala | Gly | Ile 205 | Asn | Tyr | Gly | Leu |
| Val 210 | Ala | Pro | Pro | Ala | Thr 215 | Thr | Ala | Glu | Thr | Leu 220 | Asp | Val | Gln | Met | Lys 225 |
| Gly | Glu | Phe | Tyr | Ser 230 | Glu | Asn | His | His | Asn 235 | Pro | Pro | Pro | Phe | Ala 240 | Pro |
| Pro | Val | Met | Glu 245 | Phe | Pro | Ala | Ala | His 250 | Asp | Arg | Met | Val | Tyr 255 | Leu | Gly |
| Leu | Ser | Asp 260 | Tyr | Phe | Phe | Asn | Thr 265 | Ala | Gly | Leu | Val | Tyr 270 | Gln | Glu | Ala |
| Gly | Val 275 | Leu | Lys | Met | Thr | Leu 280 | Arg | Asp | Asp | Met | Ile 285 | Pro | Lys | Glu | Ser |
| Lys 290 | Phe | Arg | Leu | Thr | Thr 295 | Lys | Phe | Phe | Gly | Thr 300 | Phe | Leu | Pro | Glu | Val 305 |
| Ala | Lys | Lys | Phe | Pro 310 | Asn | Met | Lys | Ile | Gln 315 | Ile | His | Val | Ser | Ala 320 | Ser |
| Thr | Pro | Pro | His 325 | Leu | Ser | Val | Gln | Pro 330 | Thr | Gly | Leu | Thr | Phe 335 | Tyr | Pro |
| Ala | Val | Asp 340 | Val | Gln | Ala | Phe | Ala 345 | Val | Leu | Pro | Asn | Ser 350 | Ser | Leu | Ala |
| Ser | Leu 355 | Phe | Leu | Ile | Gly | Met 360 | His | Thr | Thr | Gly | Ser 365 | Met | Glu | Val | Ser |
| Ala 370 | Glu | Ser | Asn | Arg | Leu 375 | Val | Gly | Glu | Leu | Lys 380 | Leu | Asp | Arg | Leu | Leu 385 |
| Leu | Glu | Leu | Lys | His 390 | Ser | Asn | Ile | Gly | Pro 395 | Phe | Pro | Val | Glu | Leu 400 | Leu |
| Gln | Asp | Ile | Met 405 | Asn | Tyr | Ile | Val | Pro 410 | Ile | Leu | Val | Leu | Pro 415 | Arg | Val |
| Asn | Glu | Lys 420 | Leu | Gln | Lys | Gly | Phe 425 | Pro | Leu | Pro | Thr | Pro 430 | Ala | Arg | Val |
| Gln | Leu 435 | Tyr | Asn | Val | Val | Leu 440 | Gln | Pro | His | Gln | Asn 445 | Phe | Leu | Leu | Phe |
| Gly 450 | Ala | Asp | Val | Val | Tyr 455 | Lys | | | | | | | | | |